US008871668B2

(12) United States Patent
Kobayashi et al.

(10) Patent No.: US 8,871,668 B2
(45) Date of Patent: Oct. 28, 2014

(54) IMMOBILIZED LEWIS ACID CATALYSTS COATED WITH IONIC LIQUIDS AND USE THEREOF

(75) Inventors: Shu Kobayashi, Tokyo (JP); Yuichiro Mori, Tokyo (JP); Gu Yanlong, Tokyo (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 1362 days.

(21) Appl. No.: 12/282,444

(22) PCT Filed: Mar. 12, 2007

(86) PCT No.: PCT/JP2007/054770
§ 371 (c)(1),
(2), (4) Date: Jan. 23, 2009

(87) PCT Pub. No.: WO2007/105668
PCT Pub. Date: Sep. 20, 2007

(65) Prior Publication Data
US 2009/0318729 A1    Dec. 24, 2009

(30) Foreign Application Priority Data
Mar. 10, 2006   (JP) .................................. 2006-066030

(51) Int. Cl.
| | | |
|---|---|---|
| B01J 31/22 | (2006.01) | |
| B01J 31/02 | (2006.01) | |
| B01J 31/16 | (2006.01) | |
| C07C 327/22 | (2006.01) | |
| C07C 29/40 | (2006.01) | |
| C07C 221/00 | (2006.01) | |

(52) U.S. Cl.
CPC .............. *C07C 29/40* (2013.01); *B01J 2531/36* (2013.01); *B01J 31/2256* (2013.01); *B01J 2531/54* (2013.01); *B01J 31/0254* (2013.01); *B01J 31/0252* (2013.01); *B01J 31/0284* (2013.01); *B01J 2531/96* (2013.01); *B01J 31/1633* (2013.01); *C07C 327/22* (2013.01); *B01J 31/0288* (2013.01); *B01J 2531/35* (2013.01); *C07C 221/00* (2013.01); *B01J 31/0292* (2013.01); *B01J 2531/38* (2013.01); *B01J 2231/32* (2013.01); *B01J 2231/346* (2013.01); *B01J 2231/342* (2013.01)
USPC ........................................................ 502/168

(58) Field of Classification Search
USPC ........................................................ 502/168
See application file for complete search history.

(56) References Cited

U.S. PATENT DOCUMENTS

| 6,797,853 | B2 | 9/2004 | Houzvicka et al. |
|---|---|---|---|
| 6,881,698 | B2 | 4/2005 | Bonnet et al. |
| 6,916,761 | B1 | 7/2005 | Kobayashi |
| 7,005,282 | B2 | 2/2006 | Kim et al. |
| 2002/0169071 | A1 | 11/2002 | Sauvage et al. |
| 2009/0326228 | A1 | 12/2009 | Vaultier et al. |

FOREIGN PATENT DOCUMENTS

| EP | 1184076 A1 | 3/2002 | | |
|---|---|---|---|---|
| JP | 11-244705 A | 9/1999 | | |
| JP | 2001-137710 A | 5/2001 | | |
| JP | 2002-265394 A | 9/2002 | | |
| JP | 2002-275118 A | 9/2002 | | |
| JP | 2003-512926 A | 4/2003 | | |
| JP | 2003-512926 A | * 8/2003 | ............... | B01J 31/30 |
| JP | 2003-535054 A | 11/2003 | | |
| JP | 2004-243247 A | 9/2004 | | |
| JP | 2004-269846 A | 9/2004 | | |
| JP | 2005-514033 A | 5/2005 | | |
| JP | 2005-254115 A | 9/2005 | | |
| JP | 2005-314500 A | 11/2005 | | |
| JP | 2006-500418 A | 1/2006 | | |
| WO | 01/32308 A1 | 5/2001 | | |
| WO | WO 01/32308 | * 5/2001 | ............... | B01J 31/02 |
| WO | 2005028446 A1 | 3/2005 | | |

OTHER PUBLICATIONS

Gu et al. "A Heterogeneous Silica-Supported Scandium/Ionic Liquid Catalyst System for Organic Reactions in Water" Angew. Chem. Int. Ed. 2006, pp. 7217-7220.*

Iimura et al. "Hydrophobic polymer-supported scandium catalyst for carbon—carbon bond-forming reactions in water" Tetrahedron, 2004, vol. 60, pp. 7673-7678.*

C.Decastro et al. "Immobilised Ionic Liquids as Lewis Acid Catalysts for the Alkylation of Aromatic Compounds with Dodecene," Journal of Catalysis; 2000; vol. 196; pp. 86-94.

(Continued)

*Primary Examiner* — Joseph Kosack

(74) *Attorney, Agent, or Firm* — Westerman, Hattori, Daniels & Adrian, LLP

(57) ABSTRACT

The invention provides a novel immobilized Lewis acid catalyst which exhibits high catalytic activity in an aqueous solution and which permits recovery and reuse or long-term continuous use. The invention relates to an immobilized Lewis acid catalyst comprising a solid substance and a Lewis acid supported on the surface of the solid substance by chemical bonding, wherein the surface of the solid substance and the peripheries of the Lewis acid are coated with an ionic liquid, more specifically, an immobilized Lewis acid catalyst comprising a solid substance such as silica gel or an organic polymer and a Lewis acid stable even in water which is supported on the surface of the solid substance by chemical bonding, wherein the surface of the solid substance and the peripheries of the Lewis acid are completely or partially coated with a hydrophobic ionic liquid; a process for the production of the catalyst; use thereof; and a process for the preparation of compounds with the catalyst.

16 Claims, 1 Drawing Sheet

(56) References Cited

OTHER PUBLICATIONS

H. Hagiwara et al. "Sustainable Mizoroki-Heck reaction in water: remerkably high activity of Pd(OAc)2 immobilized on reversed phase silica gel with the aid of an ionic liquid," Chem. Commun. 2005; pp. 2942-2944.

Y. Gu et al. "A Heterogeneous Silica-Supported Scandium / Ionic Liquid Catalyst System for Organic Reactions in Water," Angewandte Chem. Int'l Edision; Nov. 6, 2006; vol. 45; No. 43; pp. 7217-7220.

International Search Report of PCT/JP2007/054770, date of mailing May 22, 2007.

Notification of Transmittal of Translation of the International Preliminary Report on Patentability (Form PCT/IB/338) of International Application No. PCT/JP2007/054770 mailed Oct. 9, 2008 with Forms PCT/IPEA/409.

European Search Report dated Aug. 26, 2009, issued corresponding European Patent Application No. 07738242.2.

Yadav, J. S. et al.; "Bi(OTf)3/[bmim]BF4 as novel and reusable catalytic system for the synthesis of furan, pyrrole and thiophene derivatives"; Tetrahedron Letters, 2004, pp. 5873-5876, vol. 45.

Yadav, J. S. et al.; "Conjugate addition of indoles to alpha, beta-unsaturated ketones using Cu(OTf)2 immobilized in ionic liquids"; Tetrahedron, 2005, pp. 9541-9544, vol. 61.

Kobayashi, Shu, "Scandium Triflate in Organic Synthesis", Eur. J. Org. Chem., 1999, pp. 15-27 (13 pages).

Welton, Thomas, "Room-Temperature Ionic Liquids. Solvents for Synthesis and Catalysis", Chem. Rev. 1999, vol. 99, No. 8, pp. 2071-2083, (14 pages).

Wasserscheid, Peter et al., "Ionic Liquids—New "Solutions" for Transitions Metal Catalysis", Angew. Chem. Int. Ed., 2000, vol. 39, pp. 3772-3789 (18 pages).

Gruttadauria, Michelangelo et al., "Supported Ionic Liquids. New Recyclable Materials for the L-Proline-Catalyzed Aldol Reaction", Adv. Synth. Catal., 2006, vol. 348, pp. 82-92, (11 pages).

Jones, Christopher W. et al., "Organic-functionalized molecular sieves as shape-selective catalysts", Nature, 1998, vol. 393, pp. 52-54 (3 pages).

Huddleston, Jonathan G. et al., "Characterization and comparison of hydrophilic and hydrophobic room temperature ionic liquids incorporating the imidazolium cation", Green Chemistry, 2001, vol. 3, pp. 156-164 (9 pages).

\* cited by examiner

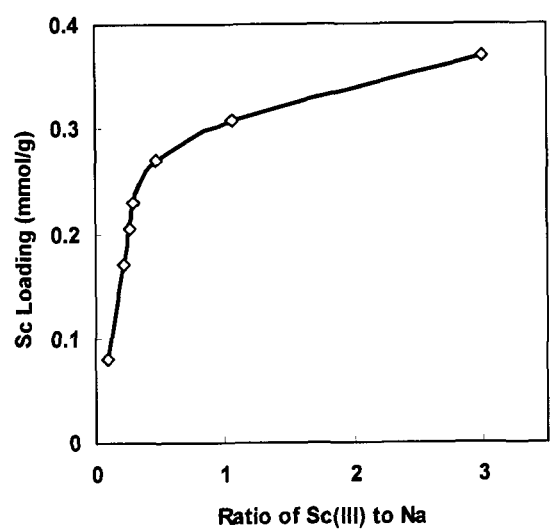

IMMOBILIZED LEWIS ACID CATALYSTS COATED WITH IONIC LIQUIDS AND USE THEREOF

TECHNICAL FIELD

The present invention relates to an immobilized Lewis acid catalyst prepared by supporting a Lewis acid on the surface of a solid substance by chemical binding, and coating the surface of the solid substance and the peripheries of the Lewis acid with an ionic liquid, as well as a use of the catalyst and a method for producing a compound using the catalyst.

BACKGROUND ART

In chemical industries, conversion of reaction solvents from organic solvents to water has been actively investigated for the purpose of cost reduction, safety, reduction of environmental loads and the like. However, there are only few examples of succeeding such conversion because of the problems of solubility of the reaction substrate or catalyst, safety and the like. In recent years, the inventors of the present invention succeeded in developing a Lewis acid catalyst which is stable even in water, and subsequently a Lewis acid catalyst integrated with a surfactant (see Patent Document 1), thereby greatly increased the possibility of carrying out synthesis reactions in water (see Non-Patent Document 1). Furthermore, the inventors of the present invention conducted investigation on the immobilization of a catalyst onto an insoluble support, for the purpose of facilitating the isolation of catalysts from products or the recovery/reuse of catalysts, and found that a Lewis acid catalyst which is bound to a hydrophobic polymer support and is stable in water, accelerates various reactions in water, compared with in an organic solvent (see Non-Patent Document 2, Patent Document 2 and Patent Document 3). Nevertheless, Lewis acid catalysts supported on organic polymers have problems such as that production of such catalysts is relatively difficult and expensive.

Meanwhile, in recent years, ionic liquids are attracting attention as a new reaction field (see Non-Patent Documents 3 and 4), and a biphasic reaction involving a solution or a gas has been recently developed, in which an ionic liquid is supported on the surface of a porous support so as to use the ionic liquid as an immobilized catalyst (see Non-patent Document 5). In addition, a method of performing a Heck reaction using a Pd/C catalyst in an ionic liquid (see Patent Document 4), a method of performing an aldol reaction using proline as a catalyst in the presence of an ionic liquid, and recovering and reusing the catalyst or solvent (see Patent Document 5), a method of using an ionic liquid as a catalyst in the isomerization of paraffinic hydrocarbons or in the production of high octane gasoline (see Patent Documents 6 and 7) and the like, have been reported. As such, ionic liquids are widely used as reaction solvents or catalysts. Furthermore, numerous improvements are also being added to the ionic liquids themselves, such as in the cases of an immobilized ionic liquid in which either the cations or the anions of the ionic liquid are immobilized (see Patent Document 8), a method for producing an ionic liquid from a Lewis acid having titanium, niobium, tantalum, tin or antimony as the base (see Patent Document 9), and the like. Also, a method of coating an enzyme with an ionic liquid and using the coated enzyme in an enzymatic reaction (see Patent Document 10), a method of using an ionic liquid as a liquid matrix in an organic reaction in a homogeneous phase (see Patent Document 11) and the like, have been reported.

However, examples of utilizing an ionic liquid phase as a hydrophobic field in reactions performed in aqueous solutions are yet to be known.

Patent Document 1: JP-A No. 11-244705
Patent Document 2: JP-A No. 2001-137710
Patent Document 3: JP-A No. 2005-254115
Patent Document 4: JP-A No. 2002-265394
Patent Document 5: JP-A No. 2002-275118
Patent Document 6: JP-A No. 2004-269846
Patent Document 7: JP-A No. 2005-314500
Patent Document 8: JP-W No. 2003-512926
Patent Document 9: JP-A No. 2003-535054
Patent Document 10: JP-A No. 2005-514033
Patent Document 11: JP-A No. 2006-500418
Non-Patent Document 1: Kobayashi, S., Eur. J. Org. Chem., 1999, 15.
Non-Patent Document 2: Iimura, S.; Manabe, K.; Kobayashi, S., Tetrahedron, 2004, 60, 7673.
Non-Patent Document 3: Welton T., et al., Chem. Reviews, 1999, 99, 2071-2083.
Non-Patent Document 4: Wasserscheid P, et al., Angewadte Chemie International Edition, 2000, 39(21), 3772-3787.
Non-Patent document 5: Gruttadauria, M.; Riela, S.; Aprile, C.; Meo, P. L.; D'Anna, F. and Noto, R., Adv. Synth. Catal., 2006, 348, 82.
Non-Patent Document 6: Jones, C. W.; Tsuji, K; Davis, M. E., Nature, 1998, 393, 52.
Non-Patent Document 7: Huddleston, J. G.; Visser, A. E.; Reichert, W. M.; Willauer, H. D.; Broker, G. A.; Rogers, R. D., Green Chem. 2001, 3, 156.

DISCLOSURE OF THE INVENTION

Problems to be Solved by the Invention

It is an object of the present invention to provide a novel immobilized Lewis acid catalyst which has a high catalytic activity in an aqueous solution, and can be recovered, reused or continuously used for a long time.

Means for Solving the Problems

The inventors of the present invention developed a Lewis acid catalyst which is stable even in water, and thus greatly increased the possibility of synthesis reactions in water (see Non-Patent Document 1). The inventors also conducted investigation on the immobilization of a catalyst onto an insoluble support, for the purpose of facilitating the isolation of catalysts from products or the recovery/reuse of catalysts, and found that a Lewis acid catalyst which is bound to a hydrophobic polymer support and is stable in water, accelerates various reactions in water, compared with in an organic solvent (see Non-Patent Document 2, Patent Document 2 and Patent Document 3). Nevertheless, Lewis acid catalysts supported on organic polymers have problems such as that production of such catalysts is relatively difficult and expensive, and thus the inventors continued their investigation. As a result, the inventors found that when an immobilized Lewis acid catalyst is coated with a hydrophobic ionic liquid, a Lewis acid catalyst which does not impair the catalytic activity in water and is reusable, can be obtained.

Thus, the present invention relates to an immobilized Lewis acid catalyst prepared by supporting a Lewis acid on the surface of a solid substance by chemical bonding, and coating the surface of the solid substance and the peripheries of the Lewis acid with an ionic liquid, and more particularly, to an immobilized Lewis acid catalyst prepared by supporting a Lewis acid which is stable even in water, on the surface of a solid substance such as silica gel or an organic polymer by chemical bonding, and coating the surface of the solid substance and the entire or a part of the peripheries of the Lewis acid with a hydrophobic ionic liquid.

The present invention also relates to a method for producing an immobilized Lewis acid coated with an ionic liquid, the method comprising mixing an immobilized Lewis acid composed of a Lewis acid supported and immobilized on the surface of a solid substance by chemical bonding, with a solution of an ionic liquid dissolved in an organic solvent, and then removing the organic solvent, and more particularly, to a method for producing an immobilized Lewis acid coated with an ionic liquid, the method comprising mixing an immobilized Lewis acid composed of a Lewis acid which is stable even in water, supported and immobilized on the surface of a hydrophobic solid substance by chemical bonding, with a solution of a hydrophobic ionic liquid dissolved in an organic solvent, and then removing the organic solvent.

Moreover, the present invention relates to a use of the immobilized Lewis acid catalyst coated with an ionic liquid according to the present invention, and a method for producing a chemical product by a chemical reaction using the catalyst.

The present invention may be described in more detail, as follows.

(1) An immobilized Lewis acid catalyst prepared by supporting a Lewis acid on the surface of a solid substance by chemical bonding, and coating the surface of the solid substance and the peripheries of the Lewis acid with an ionic liquid.

(2) The immobilized Lewis acid catalyst according to (1) above, wherein the ionic liquid is a hydrophobic ionic liquid.

(3) The immobilized Lewis acid catalyst according to (1) or (2) above, wherein the ionic liquid is an ionic liquid containing any of imidazolium, pyridinium, quaternary ammonium and quaternary phosphonium, as a cation.

(4) The immobilized Lewis acid catalyst according to any one of (1) to (3) above, wherein the ionic liquid is an ionic liquid containing any of a halide ion and trifluoromethanesulfonate, tetrafluoroborate, hexafluoroantimonate, hexafluorophosphate and bis(trifluoromethanesulfonamide) ions, as an anion.

(5) The immobilized Lewis acid catalyst according to any one of (1) to (4) above, wherein the ionic liquid is an imidazolium salt.

(6) The immobilized Lewis acid catalyst according to any one of (1) to (5) above, wherein the ionic liquid is an imidazolium salt, and is an ionic liquid in which a hydrocarbon group having 6 or more carbon atoms is bound to at least one of the two nitrogen atoms present in the imidazole ring of the imidazolium salt.

(7) The immobilized Lewis acid catalyst according to any one of (1) to (6) above, wherein the Lewis acid is a Lewis acid which is stable even in water.

(8) The immobilized Lewis acid catalyst according to any one of (1) to (7) above, wherein the Lewis acid is a rare earth metal salt or a bismuth salt.

(9) The immobilized Lewis acid catalyst according to any one of (1) to (8), wherein the Lewis acid is a trifluoromethanesulfonic acid salt of a rare earth metal, or a trifluoromethanesulfonic acid salt of bismuth.

(10) The immobilized Lewis acid catalyst according to (9) above, wherein the rare earth metal is any of scandium, yttrium and ytterbium.

(11) The immobilized Lewis acid catalyst according to any one of (1) to (10) above, wherein the solid substance supporting the Lewis acid on the surface is any of a metal oxide, activated carbon, a synthetic organic polymer and glass.

(12) The immobilized Lewis acid catalyst according to any one of (1) to (11) above, wherein the solid substance supporting the Lewis acid on the surface is any of silica gel, crosslinked polystyrene, crosslinked polyethylene and crosslinked perfluoropolyethylene.

(13) The immobilized Lewis acid catalyst according to any one of (1) to (12) above, wherein the solid substance supporting the Lewis acid on the surface is silica gel.

(14) The immobilized Lewis acid catalyst according to any one of (1) to (13) above, wherein the Lewis acid is chemically bound to a sulfonic acid group or sulfonamide group that is bound to the surface of the solid substance directly or through a low molecular weight organic compound.

(15) The immobilized Lewis acid catalyst according to any one of (1) to (14) above, wherein the solid supporting the Lewis acid on the surface is silica gel, the silica gel is bound to a low molecular weight organic compound through a siloxane bond (Si—O—Si), the low molecular weight organic compound further has a sulfonic acid group, and the Lewis acid is chemically bound to the sulfonic acid group.

(16) A method for producing an immobilized Lewis acid coated with an ionic liquid, the method comprising mixing an immobilized Lewis acid composed of a Lewis acid which is stable even in water, supported and immobilized on the surface of a solid substance by chemical bonding, with a solution of a hydrophobic ionic liquid dissolved in an organic solvent, and then removing the organic solvent.

(17) The method according to (16) above, wherein the Lewis acid is a trifluoromethanesulfonic acid salt of a rare earth metal, or a trifluoromethanesulfonic acid salt of bismuth.

(18) Use of the immobilized Lewis acid catalyst according to any one of (1) to (15) above, in a Lewis acid-catalyzed chemical reaction performed in water or a water-containing organic solvent.

(19) The use according to (18) above, wherein the Lewis acid-catalyzed chemical reaction performed in water or a water-containing organic solvent is any chemical reaction selected from the group consisting of an aldol reaction, a Mannich type reaction, a Diels-Alder reaction, an allylation reaction and a Michael reaction.

(20) A method for producing a chemical substance by a Lewis acid-catalyzed chemical reaction performed in water or a water-containing organic solvent, in the presence of the immobilized Lewis acid catalyst according to any one of (1) to (15).

(21) The method according to (20) above, wherein the Lewis acid-catalyzed chemical reaction performed in water or a water-containing organic solvent is any chemical reaction selected from the group consisting of an aldol reaction, a Mannich type reaction, a Diels-Alder reaction, an allylation reaction and a Michael reaction.

As the immobilized Lewis acid composed of a Lewis acid which is stable even in water, supported on the surface of a solid substance according to the present invention, the Lewis acid may be bound to the surface of the solid substance directly or through a group having a functional group such as a spacer.

As the Lewis acid of the present invention, a conventional Lewis acid such as a metal Lewis acid formed from a salt of Al, B, Ti, Zr, Sn, Zn, Ga, Bi, Sb, Cd, V, Mo, W, Mn, Fe, Cu, Co, Pb, Ni, Hf, Ag, a rare earth metal and the like may be favorable, but in the case where a reaction in water is intended, a Lewis acid which is stable even in water is preferred. Such Lewis acid which is stable even in water includes a Lewis acid represented by the following formula:

$$MX_n$$

wherein M represents a rare earth metal or bismuth; X represents an anion; and n represents an integer corresponding to the valence of M. The rare earth metal is preferably selected from the group of rare earth elements including elements such as, for example, Sc, Yb, Sm, Y and Nd, and Sc is particularly preferred. Therefore, the metal element of the Lewis acid according to the present invention is preferably a metal element selected from the group consisting of Sc, Yb, Sm, Y, Nd and Bi, and Sc or Bi is particularly preferred. The anion includes anions such as $R^a$—COO$^-$, $R^a$—SO$_3^-$, $R^a$—OSO$_3^-$, $R^a$—OPO$_3^{2-}$ and $R^a$—(phenyl) O$^-$ (wherein $R^a$ represents a hydrocarbon group which may be substituted) for example, but among them, $R^a$—SO$_3^-$ is preferred. Furthermore, a preferred $R^a$ group includes a straight-chained or branched alkyl group having 1 to 8, preferably 1 to 4, carbon atoms in which one or more hydrogen atoms are substituted with fluorine atoms, or a phenyl group and the like. A preferred anion according to the present invention includes a perfluoroalkanesulfonic acid anion. A particularly preferred anion includes a trifluoromethanesulfonic acid ion (CF$_3$SO$_3^-$(OTf).

Specific examples of the preferred Lewis acid according to the present invention include, for example, trifluoromethanesulfonic acid salts of scandium, yttrium, ytterbium, bismuth and the like. A particularly preferred Lewis acid includes a trifluoromethanesulfonic acid salt of scandium or bismuth and the like.

The solid substance for supporting the Lewis acid according to the present invention is not particularly limited as long as the solid substance is stable in water and insoluble in water, and has a functional group capable of chemical bonding, on the surface of the solid substance, and various materials such as metal oxides, activated carbon, synthetic organic polymers and glass can be used. Preferred solid substances of the present invention include silica gel, crosslinked polystyrene, crosslinked polyethylene, crosslinked perfluoropolyethylene and the like.

The method of immobilizing the above-described Lewis acid onto the solid substance according to the present invention is not particularly limited, as long as it is a method based on chemical bonding such as covalent bonding, ionic bonding or coordinate bonding. The Lewis acid may be directly bound to the surface of the solid substance, but it is preferable to use a method of binding the Lewis acid through a spacer group formed from an appropriate low molecular weight organic compound. The appropriate low molecular weight organic compound includes benzenesulfonic acid, alkylbenzenesulfonic acid and the like, for example. Such low molecular weight organic compound can be reacted with the functional group at the surface of the solid substance to form chemical bonding. For example, in the case of using a solid substance having a benzene ring, such as polystyrene or a divinylbenzene-styrene copolymer, as the solid substance, the low molecular weight organic compound can be bound into the benzene ring of these polymers, by an electrophilic substitution reaction such as a Friedel-Craft reaction. As for specific examples of such case, Patent Documents 1 and 2 can be referred to. Here, the descriptions of Patent Documents 1 and 2 are incorporated in the present specification as reference.

Furthermore, in the case of using silica gel as the solid substance, chemical bonding can be formed with the silanol group at the surface of the silica gel. For example, when a silyl compound such as alkyl or aryltrialkoxysilane is used, a Si—O—Si-alkyl or aryl bond can be formed at the surface of the silica gel.

Furthermore, such binding of the Lewis acid of the present invention with the low molecular weight organic compound as a spacer, can be achieved through ionic bonding with an acidic group carried by the low molecular weight organic compound. For example, when the acidic group carried by the low molecular weight organic compound is a sulfonic acid group, binding can be achieved by neutralizing the acidic group with a base, and then mixing the resultant with the Lewis acid of the present invention.

These methods can be carried out in an appropriate organic solvent.

The amount of immobilization of the Lewis acid to the solid substance is not particularly limited, but the amount may be usually 0.01 mmol to 1 mmol, and preferably 0.05 mmol to 0.5 mmol, of the Lewis acid based on 1 g of the solid substance.

The ionic liquid according to the present invention is a salt composed of an organic cation species and an anion species, and may be exemplified by a compound having a lower melting point than conventional salts, and maintaining the liquid state at a melting point of 150° C. or below, preferably 80° C. or below, and more preferably 0° C. Examples of such ionic liquid include alkyl-substituted imidazolium salts, alkyl-substituted pyridinium salts, quaternary ammonium salts, quaternary phosphonium salts, tertiary sulfonium salts, and the like, and as the ionic liquid of the present invention, alkyl-substituted imidazolium salts, alkyl-substituted pyridinium salts and quaternary ammonium salts are preferred, while among them, alkyl-substituted imidazolium salts are preferred.

The organic cation species of the ionic liquid of the present invention includes, an imidazolium cation in which two nitrogen atoms of an imidazole ring are bound to the same alkyl group or to different alkyl groups, a pyridinium cation in which a nitrogen atom on a pyridine ring is bound to an alkyl group, an ammonium cation in which identical or different four alkyl groups are bound to a nitrogen atom, a phosphonium cation in which identical or different four alkyl groups are bound to a phosphorus atom, a sulfonium cation in which identical or different three alkyl groups are bound to a sulfur atom, and the like. The cationic species which are preferable as the ionic liquid of the present invention includes, an imidazolium cation in which two nitrogen atoms of an imidazole ring are bound to the same alkyl group or to different alkyl groups, a pyridinium cation in which a nitrogen atom on a pyridine ring is bound to an alkyl group, an ammonium cation in which identical or different four alkyl groups are bound to a nitrogen atom and the like, while a more preferred cation species may be exemplified by an imidazolium cation in which two nitrogen atoms of an imidazole ring are bound to the same alkyl group or to different alkyl groups.

The alkyl group in these cation species includes, a straight-chained or branched alkyl group having 1 to 12 carbon atoms, and preferably a straight-chained alkyl group having 1 to 10 carbon atoms. Specifically, for example, a methyl group, an ethyl group, an n-propyl group, an n-butyl group, an n-pentyl group, an n-hexyl group, an n-heptyl group, an n-octyl group, an n-decyl group and the like may be included.

The anion species of the ionic liquid of the present invention includes, a hexafluoroantimonate anion, a hexafluorophosphate anion, a tetrafluoroborate anion, a chlorine anion, a bromine anion, an iodine anion, an alkanesulfonate anion, a perfluoroalkanesulfonate anion and the like.

The ionic liquid of the present invention is obtained by appropriately combining these anion species and the above-mentioned cation species. For example, imidazolium hexafluoroantimonate, imidazolium hexafluorophosphate, imidazolium tetrafluoroborate, imidazolium chloride, imidazolium bromide, imidazolium iodide, imidazolium alkanesulfonate; pyridinium hexafluoroantimonate, pyridinium hexafluorophosphate, pyridiniumtetrafluoroborate, pyridinium chloride, pyridinium bromide, pyridinium iodide, pyridinium alkanesulfonate; ammonium hexafluoroantimonate, ammonium hexafluorophosphate, ammonium tetrafluoroborate, ammonium chloride, ammonium bromide, ammonium iodide, ammonium alkanesulfonate; phosphonium hexafluoroantimonate, phosphonium hexafluorophosphate, phosphonium tetrafluoroborate, phosphonium chloride, phosphonium bromide, phosphonium iodide, phosphonium alkanesulfonate and the like may be included.

The ionic liquid of the present invention that has been described so far can be produced by a known method, or a commercially available product may be used. Furthermore, the ionic liquid can also be produced according to the method described in Non-Patent Document 7.

As the coating method of the present invention, production can be achieved by dissolving anionic liquid in an organic solvent, mixing this solution with the immobilized Lewis acid catalyst of the present invention described above, and then removing the organic solvent.

The organic solvent in this method is not particularly limited as long as the solvent is volatile and can dissolve an ionic liquid, and for example, ester-based solvents such as ethyl acetate, ether-based solvents such as dimethoxyethane and THF, ketone-based solvents such as acetone, halogenated hydrocarbons such as dichloroethane, and the like may be included.

The ionic liquid is dissolved in these organic solvents, and to this solution, the immobilized Lewis acid catalyst of the present invention is added and mixed with stirring. This operation is usually performed at room temperature, but the system may be appropriately cooled or may also be heated. The amount of the ionic liquid used may be 10 to 200% by mass, preferably 10 to 100% by mass, 10 to 80% by mass, 30 to 100% by mass, or 30 to 80% by mass, based on the mass of the immobilized Lewis acid catalyst of the present invention. These are sufficiently mixed, and then the organic solvent is removed. The method of removing the organic solvent is performed by distilling off the solvent at normal pressure or under reduced pressure. When the organic solvent is completely distilled off, a solid dried immobilized Lewis acid catalyst of the present invention is obtained. The obtained immobilized Lewis acid catalyst of the present invention is coated with the added ionic liquid. If surplus ionic liquid, that is, ionic liquid that is not used in the coating, is present, the coated immobilized Lewis acid catalyst of the present invention can be obtained by eliminating the excess ionic liquid.

The immobilized Lewis acid catalyst coated with an ionic liquid of the present invention not only has a catalytic activity as a Lewis acid in a non-homogeneous reaction system, but also has a good catalyst recovery rate, and can be reused. Even if the immobilized Lewis acid catalyst were expensive, the catalyst can be repeatedly used, and thus can be used as a practical catalyst.

In the reaction using the immobilized Lewis acid catalyst coated with an ionic liquid of the present invention, the solvent is not particularly limited as long as the solvent does not dissolve an ionic liquid, but water or a water-containing organic solvent is particularly suitable.

Furthermore, the present invention is to provide a use of the immobilized Lewis acid catalyst coated with an ionic liquid of the present invention, as a Lewis acid catalyst for various chemical reactions.

Examples of such chemical reactions include an aldol reaction, a Mannich type reaction, a Diels-Alder reaction, an allylation reaction, a Michael reaction, and the like.

In addition, the present invention is to provide a method for producing chemical substances by various chemical reactions using the immobilized Lewis acid catalyst coated with an ionic liquid of the present invention. This method of the present invention can be applied to, for example, an aldol reaction, a Mannich type reaction, a Diels-Alder reaction, an allylation reaction, a Michael reaction, and the like, and the present invention is to provide a method for producing chemical substances that can be produced by these reactions.

Effects of the Invention

The present invention is to provide a practical immobilized Lewis catalyst which can be easily recovered after use, and can be repeatedly used in various chemical reactions, by coating an immobilized Lewis acid catalyst, which is difficult to produce and expensive, with an ionic liquid. The immobilized Lewis acid catalyst coated with an ionic liquid of the present invention can be applied to various chemical reactions that are carried out in the presence of a Lewis acid catalyst, is stable against water, and is effective in Lewis acid catalyzed reactions that are performed in water or a water-containing organic solvent, thus making it possible to perform environmentally friendly chemical reactions.

BRIEF DESCRIPTION OF THE DRAWINGS

FIG. 1 shows a graph plotted, in the case where scandium triflate is used as a Lewis acid in the immobilized Lewis acid catalyst coated with an ionic liquid of the present invention, for the ratio of added scandium triflate (ratio with respect to sodium salt) (horizontal axis) and the loading rate (ratio) of scandium in a silica gel supporting scandium (vertical axis).

The present invention is illustrated in more detail by the following Examples, but should not be construed to be limited thereto.

In these Examples, silica gel used was Davisil™ 643. For water, distilled water was used after deaeration, and reactions were performed in argon. Silicon enolate was synthesized according to the literature (see Non-Patent Document 6). The ionic liquid was synthesized according to an existing method (see Non-Patent Document 7). As for reagents other than those, commercial products were purchased and used after purification as necessary.

PRODUCTION EXAMPLE 1

Immobilization of Scandium onto Silica Gel

Scandium was immobilized onto silica gel according to the reaction scheme shown in the following.

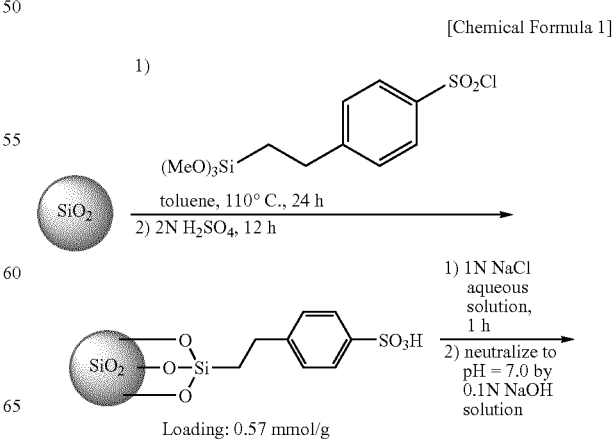

[Chemical Formula 1]

-continued

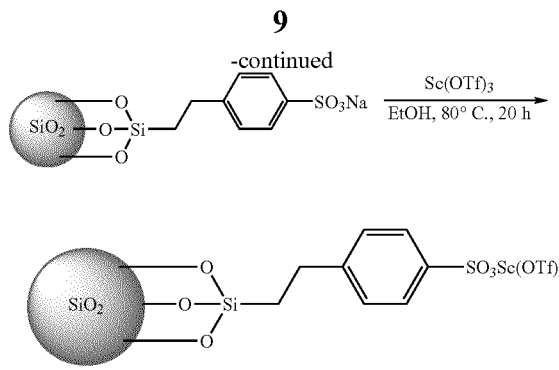

TABLE 1

| Sc/Na (M/M) | Sc Loading (mmol/g) |
| --- | --- |
| 0.99 | 0.08 |
| 0.21 | 0.17 |
| 0.26 | 0.20 |
| 0.30 | 0.23 |
| 0.47 | 0.28 |
| 1.05 | 0.31 |
| 3.00 | 0.37 |

PRODUCTION EXAMPLE 2

Immobilization of Bismuth onto Silica Gel

The same operation as in Production Example 1 was performed, except that bismuth triflate (0.33 mmol) was used instead of the scandium triflate in Production Example 1, and the amount of use of the sodium arylsulfonate-immobilized silica gel was set to 0.58 g, and thus a bismuth-bound silica gel was obtained. The yield was 0.58 g, and the bismuth loading amount was 0.25 mmol/g.

EXAMPLE 1

Coating of Surface of Silica Gel Supporting Scandium with Ionic Liquid

The silica gel supporting scandium (50 mg) produced in Production Example 1 was mixed with an ethyl acetate solution (0.25 ml) of 1-butyl-3-decylimidazolium hexafluoroantimonate (25 mg) for 10 minutes at room temperature. Ethyl acetate was distilled off under reduced pressure, and dried under reduced pressure for 20 minutes, to thus obtain a silica gel-supported scandium catalyst coated with an ionic liquid as a dry powder. Yield 65 mg. The amount of supported scandium was 0.21 mmol/g.

EXAMPLE 2

Coating of Surface of Silica Gel Supporting Bismuth with Ionic Liquid

The same operation as in Example 1 was performed using the silica gel supporting bismuth produced in Production Example 2 in place of the silica gel supporting scandium of Example 1, and thus a silica gel-supported bismuth catalyst coated with an ionic liquid was obtained. Yield 75 mg. The amount of supported bismuth was 0.17 mmol/g.

EXAMPLE 3

Mukaiyama-aldol reaction represented by following reaction scheme, using silica gel-supported scandium catalyst coated with ionic liquid (Chlorosulfonylphenyl)ethyltriethoxysilane (5 g) was refluxed together with silica gel (6.2 g) in toluene (30 ml) for 24 hours. The insoluble was collected by filtration and washed with toluene, and then the solvent was distilled off under reduced pressure. Subsequently, the resultant was treated in a 2 M aqueous solution of sulfuric acid at 80° C. for 12 hours. The insoluble was collected by filtration and dried under reduced pressure, to obtain 6.2 g of sulfonic acid group-bound silica gel. 1 g of this silica gel had 0.57 millimoles of sulfonic acid groups incorporated. This (6.2 g) was suspended in 1 M saline (200 ml), and the suspension was neutralized by adding a 0.1M sodium hydroxide solution dropwise. The reaction product was filtered, and the insoluble was washed with water and then dried under reduced pressure. The obtained silica gel having sodium arylsulfonate immobilized (0.52 g) and scandium triflate (68.5 mg) were added to ethanol (6.2 ml), and the mixture was refluxed for 20 hours. The reaction product was filtered, and the insoluble was washed with ethanol and then dried under reduced pressure, to obtain a silica gel having scandium bis(trifluoromethanesulfonate) bound through arylsulfonic acid. The yield was 0.52 g, and the scandium loading amount was 0.28 mmol/g.

The ratio of scandium triflate with respect to sodium arylsulfonate on the silica gel was changed as indicated in the following Table 1, and the same treatment as described in the above Production Example 1 was performed. As a result, silica gels supporting scandium with different loading rates of scandium triflate were produced.

The ratio of added scandium triflate (ratio with respect to sodium salt) and the loading rate of scandium in the produced silica gel supporting scandium are presented in the following Table 1. Furthermore, a graph summarizing these results is shown in FIG. 1. The horizontal axis of FIG. 1 represents the ratio of added scandium triflate (ratio with respect to sodium salt), while the vertical axis represents the loading rate (ratio) of scandium in the silica gel supporting scandium.

[Chemical Formula 2]

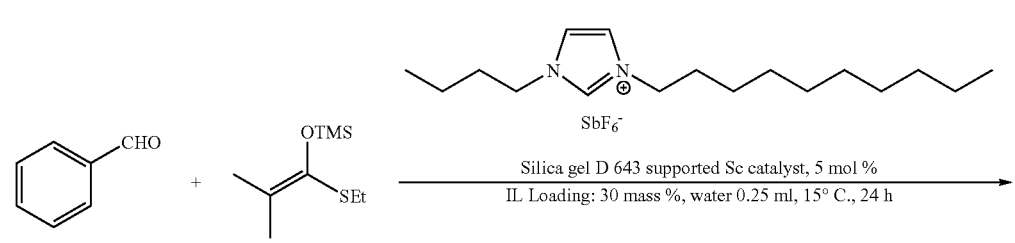

Water (0.25 ml) was added to the silica gel supporting scandium produced in Example 1 (65 mg), and while stirring, benzaldehyde (0.25 mmol) and 1-ethylthio-1-trimethylsiloxy-2-methyl-1-propene (0.38 mmol) were continuously added. The mixture was stirred at 15° C. for 24 hours. The mixture was extracted four times by a decantation method using hexane, the solvent was distilled off under reduced pressure, and then the residue was purified by silica gel thin layer chromatography, to obtain the target product, 3-hydroxy-2,2-dimethyl-3-phenylthiopropionate, as a colorless oil. Yield 97%.

$^1$H NMR (CDCl$_3$) δ;

1.12 (3H, s), 1.22 (3H, s), 1.26 (3H, t, J=7.4 Hz), 2.89 (2H, q, J=7.4 Hz), 2.96 (1H, brs), 4.94 (1H, s), 7.27-7.35 (5H, m);

$^{13}$C NMR (CDCl$_3$) δ;

14.4, 19.0, 23.3, 23.7, 54.3, 78.9, 127.78, 127.80, 139.9, 208.0

The same reaction was performed using a recovered silica gel supporting scandium, and the same target product was obtained at a yield of 95%.

COMPARATIVE EXAMPLE 1

The method described in Example 3 was carried out in the same manner as in Example 3, using a catalyst produced by mechanically coating silica gel with an ionic liquid and scandium triflate, in place of the silica gel supporting scandium.

As a result, the target product was obtained at a yield of 78%, but the catalyst could not be recovered.

From this, it has been demonstrated that since the immobilized Lewis acid catalyst of the present invention is supported by covalent bonding, there is a measurable improvement in the yield, and also, the catalyst is excellent even from the viewpoints of recovery and reuse of the catalyst. Moreover, since a sufficient catalytic activity is maintained even after reuse, the immobilized Lewis acid catalyst of the present invention can be said to be very stable.

EXAMPLE 4

Mukaiyama-Aldol Reaction Using Silica Gel-Supported Bismuth Catalyst Coated with Ionic Liquid The same operation as in Example 3 was performed, except that the silica gel supporting bismuth produced in Example 2 (50 mg) was used instead of the silica gel supporting scandium, and thus 3-hydroxy-2,2-dimethyl-3-phenylthiopropionate was obtained. Yield 84%.

EXAMPLE 5

Three-Component Mannich Type Reaction Represented by Following Reaction Scheme, Using Silica Gel-Supported Scandium Catalyst Coated with Ionic Liquid

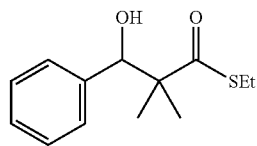

[Chemical Formula 3]

Water (0.25 ml) was added to the silica gel supporting scandium produced in Example 1 (75 mg), and while stirring, benzaldehyde (0.125 mmol) and o-anisidine (0.125 mmol) and 1-cyclohexenyloxytrimethylsilane (0.25 mmol) were continuously added. The mixture was stirred at room temperature for 24 hours. The mixture was extracted four times by a decantation method using a mixture of ethyl acetate-hexane (1:1), the solvent was distilled off under reduced pressure, and then the residue was purified by silica gel thin layer chromatography, to obtain the target product, 2-(phenyl-N-(2-methoxyphenyl)aminomethyl)cyclohexanone at a syn/anti ratio of 53/47. Yield 92%.

$^1$H NMR (CDCl$_3$) δ;

1.55-2.10 (m, 6H), 2.24-2.44 (m, 2H), 2.76-2.81 (m, 1H), 3.84 (s, 3H), 4.70 (minor, d, 1H, J=7.6 Hz), 4.87 (d, major, 1H, J=4.4 Hz), 4.80-5.20 (brs, 1H), 6.38-6.79 (m, 4H), 7.16-7.39 (m, 5H);

$^{13}$C NMR (CDCl$_3$) δ;

23.6, 24.8, 27.0, 27.8, 28.4, 30.9, 41.6, 42.0, 42.3, 53.70, 55.4, 55.5, 56.4, 57.0, 57.3, 57.5, 109.3, 109.4 110.4, 110.9, 111.4, 115.0, 116.6, 118.4, 121.0, 121.1, 126.9, 127.1, 127.3, 128.3, 128.4, 128.9, 137.0, 137.3, 141.7, 142.0, 147.1, 210.7, 212.2.

EXAMPLE 6

Allylation Reaction Represented by Following Reaction Scheme, Using Silica Gel-Supported Scandium Catalyst Coated with Ionic Liquid

[Chemical Formula 4]

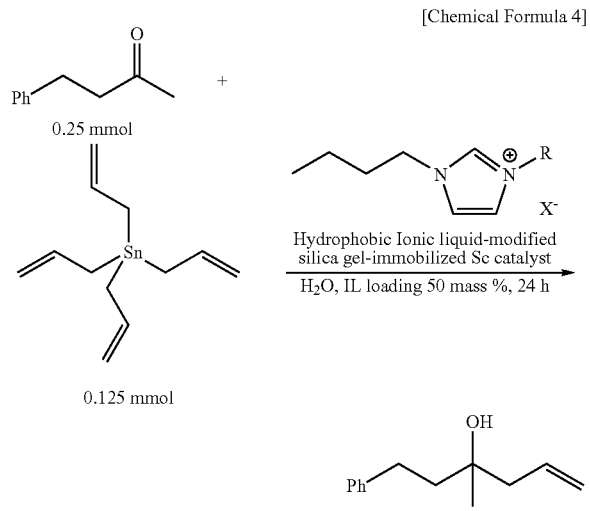

The same method as in Example 1 was carried out using 1-butyl-3-methylimidazolium hexafluorophosphate (25 mg) was used instead of 1-butyl-3-decylpyridinium hexafluoroantimonate (25 mg), and thus a silica gel-supported scandium catalyst coated with an ionic liquid was obtained. Yield 75 mg. The amount of supported scandium was 0.23 mmol/g.

Water (0.25 ml) was added to this silica gel supporting scandium (75 mg), and while stirring, 4-phenyl-2-butanone (0.25 mmol) and tetraallyltin (0.125 mmol) were continuously added. The mixture was stirred at 40° C. for 24 hours. The mixture was returned to room temperature, and then was extracted four times by a decantation method using hexane. The solvent was distilled off under reduced pressure, and then the residue was purified by silica gel thin layer chromatography, to obtain the target product, 1-phenyl-3-buten-1-ol. Yield 98%.

INDUSTRIAL APPLICABILITY

The present invention provides an immobilized Lewis acid catalyst coated with an ionic liquid, which catalyst is stable in water, has a good recovery rate, and can be reused, and provides a Lewis acid catalyst which not only maintains the activity as a Lewis acid, but also can be repeatedly used and is practical. Furthermore, since the catalyst can be used in those chemical reactions using water as the solvent, industrial usage thereof is possible without generating waste organic solvent, and thus the catalyst is useful in various chemical industries.

Therefore, the present invention has industrial applicability in chemical industries, particularly in various industries concerning organic compounds, such as organic synthesis industry, pharmaceutical industry or agrochemical industry.

The invention claimed is:

1. An immobilized Lewis acid catalyst, comprising:
   a Lewis acid supported on the surface of a solid substance by chemical bonding, and
   an ionic liquid comprising a cation and an anion, the ionic liquid coating the surface of the solid substance and the peripheries of the Lewis acid without being covalently-immobilized on the surface of the solid substance and the peripheries of the Lewis acid,
   wherein the Lewin acid is a rare earth metal of bismuth salt, and
   wherein the Lewin acid is chemically bound to a sulfonic acid group or sulfonamide group that is directly bound to the surface of the solid substance or is bound to the surface of the solid substance through a low molecular weight organic compound.

2. The immobilized Lewis acid catalyst according to claim 1, wherein the ionic liquid is a hydrophobic ionic liquid.

3. The immobilized Lewis acid catalyst according to claim 1, wherein the ionic liquid is an ionic liquid containing any of imidazolium, pyridinium, quaternary ammonium and quaternary phosphonium, as the cation.

4. The immobilized Lewis acid catalyst according to claim 1, wherein the ionic liquid is an ionic liquid containing any of a halide ion, trifluoromethanesulfonate, tetrafluoroborate, hexafluoroantimonate, hexafluorophosphate and bis(trifluoromethanesulfonamide) ions, as the anion.

5. The immobilized Lewis acid catalyst according to claim 1, wherein the ionic liquid is an imidazolium salt.

6. The immobilized Lewis acid catalyst according to claim 1, wherein the ionic liquid is an imidazolium salt, and is an ionic liquid in which a hydrocarbon group having 6 or more carbon atoms is bound to at least one of the two nitrogen atoms present in the imidazole ring of the imidazolium salt.

7. The immobilized Lewis acid catalyst according to claim 1, wherein the Lewis acid is a trifluoromethanesulfonic acid salt of a rare earth metal, or a trifluoromethanesulfonic acid salt of bismuth.

8. The immobilized Lewis acid catalyst according to claim 7, wherein the rare earth metal is any of scandium, yttrium and ytterbium.

9. The immobilized Lewis acid catalyst according to claim 1, wherein the solid substance supporting the Lewis acid on the surface is any of a metal oxide, activated carbon, a synthetic organic polymer and glass.

10. The immobilized Lewis acid catalyst according to claim 1, wherein the solid substance supporting the Lewis acid on the surface is any of silica gel, crosslinked polystyrene, crosslinked polyethylene and crosslinked perfluoropolyethylene.

11. The immobilized Lewis acid catalyst according to claim 1, wherein the solid substance supporting the Lewis acid on the surface is silica gel.

12. The immobilized Lewis acid catalyst according to claim 1, wherein the solid supporting the Lewis acid on the surface is silica gel, the silica gel is bound to the low molecular weight organic compound through a siloxane bond (Si—O—Si), the low molecular weight organic compound further has a sulfonic acid group, and the Lewis acid is chemically bound to the sulfonic acid group.

13. A method for producing an immobilized Lewis acid coated with an ionic liquid, the method comprising:
   supporting and immobilizing a Lewis acid on the surface of a solid substance by chemical bonding via a sulfonic acid group or sufonamide group that is directly bound to the surface of the solid substance or bound to the surface of the solid substance through a low molecular weight organic coumpound, then
   mixing the supported and immobilized Lewis acid with a solution of a hydrophobic ionic liquid dissolved in an organic solvent to form a liquid phase on the surface of the solid substance and on the peripheries of the Lewis acid, the liquid phase comprising the hydrophobic ionic liquid which is not covalently-immobilized on the surface of the solid substance and on the peripheries of the Lewis acid, the hydrophobic ionic liquid comprising a cation and an anion, and then
removing the organic solvent,
wherein the Lewis acid is a rare earth metal salt or a bismuth salt.

14. The method according to claim 13, wherein the Lewis acid is a trifluoromethanesulfonic acid salt of a rare earth metal, or a trifluoromethanesulfonic acid salt of bismuth.

15. A method for producing a chemical substance by a Lewis acid-catalyzed chemical reaction performed in water or a water-containing organic solvent, in the presence of the immobilized Lewis acid catalyst according to claim 1.

16. The method according to claim 15, wherein the Lewis acid-catalyzed chemical reaction performed in water or a water-containing organic solvent is any chemical reaction selected from the group consisting of an aldol reaction, a Mannich type reaction, a Diels-Alder reaction, an allylation reaction and a Michael reaction.

* * * * *